(12) United States Patent
Kuechler et al.

(10) Patent No.: US 9,365,474 B2
(45) Date of Patent: Jun. 14, 2016

(54) PROCESSES FOR PRODUCING PHENOL

(75) Inventors: Keith Holroyd Kuechler, Friendswood, TX (US); Francisco Manuel Benitez, Cypress, TX (US); Kun Wang, Bridgewater, NJ (US); James R. Lattner, LaPorte, TX (US); Christopher Lynn Becker, Manhattan, KS (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 93 days.

(21) Appl. No.: 13/816,548

(22) PCT Filed: Aug. 16, 2011

(86) PCT No.: PCT/US2011/047845
§ 371 (c)(1),
(2), (4) Date: May 13, 2013

(87) PCT Pub. No.: WO2012/036826
PCT Pub. Date: Mar. 22, 2012

(65) Prior Publication Data
US 2013/0225866 A1    Aug. 29, 2013

Related U.S. Application Data

(60) Provisional application No. 61/382,788, filed on Sep. 14, 2010.

(51) Int. Cl.
| | |
|---|---|
| C07C 2/74 | (2006.01) |
| C07C 31/08 | (2006.01) |
| C07C 37/08 | (2006.01) |
| C07C 37/86 | (2006.01) |
| C07C 407/00 | (2006.01) |
| C07C 45/53 | (2006.01) |
| C07C 45/85 | (2006.01) |

(52) U.S. Cl.
CPC . *C07C 31/08* (2013.01); *C07C 2/74* (2013.01); *C07C 37/08* (2013.01); *C07C 37/86* (2013.01); *C07C 45/53* (2013.01); *C07C 45/85* (2013.01); *C07C 407/00* (2013.01); *C07C 2101/14* (2013.01)

(58) Field of Classification Search
CPC ........ C07C 37/86; C07C 37/08; C07C 45/53; C07C 45/85; C07C 2/74; C07C 31/08; C07C 407/00; C07C 2101/14
USPC ....................................................... 568/342
See application file for complete search history.

(56) References Cited

U.S. PATENT DOCUMENTS

| | | |
|---|---|---|
| 3,140,243 A | 7/1964 | Feder et al. |
| 3,140,318 A | 7/1964 | Sodomann et al. |
| 3,316,302 A | 4/1967 | Steeman et al. |
| 3,322,651 A | 5/1967 | Nielsen |
| 3,442,958 A | 5/1969 | Choo |
| 3,692,845 A | 9/1972 | Cheema et al. |
| 3,793,383 A | 2/1974 | Johnson et al. |
| 3,933,916 A | 1/1976 | Lejeune et al. |
| 4,021,490 A | 5/1977 | Hudson |
| 4,122,125 A | 10/1978 | Murtha et al. |
| 4,147,726 A * | 4/1979 | Wu ................................ 568/342 |
| 4,169,857 A * | 10/1979 | Murtha ......................... 568/342 |
| 4,282,383 A | 8/1981 | Dai et al. |
| 4,298,765 A | 11/1981 | Cochran et al. |
| 4,328,372 A | 5/1982 | Wu |
| 4,358,618 A | 11/1982 | Sifniades et al. |
| 5,064,507 A | 11/1991 | O'Donnell et al. |
| 5,066,373 A | 11/1991 | Levy et al. |
| 5,254,751 A | 10/1993 | Zakoshansky |
| 5,283,376 A | 2/1994 | Dyckman et al. |
| 6,037,513 A | 3/2000 | Chang et al. |
| 6,201,157 B1 | 3/2001 | Keenan |
| 6,388,144 B1 | 5/2002 | Wijesekera et al. |
| 6,965,056 B1 | 11/2005 | Taggart, II et al. |
| 7,002,048 B2 | 2/2006 | Wijesekera et al. |
| 7,205,442 B2 | 4/2007 | Payne |
| 7,579,511 B1 | 8/2009 | Dakka et al. |
| 2003/0163007 A1 | 8/2003 | Dyckman et al. |
| 2006/0211890 A1 | 9/2006 | Fodor |
| 2007/0032681 A1 | 2/2007 | Walsdorff et al. |
| 2007/0276156 A1 | 11/2007 | Matsumura et al. |
| 2011/0037022 A1 | 2/2011 | Dakka et al. |
| 2011/0105805 A1 | 5/2011 | Buchanan et al. |
| 2011/0301387 A1 | 12/2011 | Wang et al. |

FOREIGN PATENT DOCUMENTS

| | | | |
|---|---|---|---|
| WO | 2009/025939 | 2/2009 | |
| WO | 2009/058527 | 5/2009 | |
| WO | 2009/058531 | 5/2009 | |
| WO | 2009/128984 | 10/2009 | |
| WO | WO2010098916 | * 9/2010 | .............. C07C 37/08 |

OTHER PUBLICATIONS

Schmidt, Robert J., "*Industrial catalytic processes—phenol production,*" Applied Catalysis A: General, 2005, vol. 280, p. 89-103.

* cited by examiner

Primary Examiner — Paul A Zucker
Assistant Examiner — Mark Luderer
(74) *Attorney, Agent, or Firm* — Stephen A. Baehl

(57) ABSTRACT

Disclosed herein are processes for producing phenol. The processes include oxidizing cyclohexylbenzene to produce an oxidation composition comprising cyclohexyl-1-phenyl-1-hydroperoxide. The cyclohexyl-1-phenyl-1-hydroperoxide in the oxidation composition may undergo a cleavage reaction to produce a cleavage reaction mixture comprising phenol, cyclohexanone and at least one contaminant. The cleavage reaction mixture may be contacted with a basic material to convert at least a portion of the contaminant to a converted contaminant, thereby producing a modified reaction mixture.

15 Claims, 1 Drawing Sheet

PROCESSES FOR PRODUCING PHENOL

PRIORITY CLAIM

This application is a National Stage Application of International Application No. PCT/US2011/047845 filed Aug. 16, 2011, which claims priority to and the benefit of U.S. Provisional Application Ser. No. 61/382,788, which was filed Sep. 14, 2010, and is incorporated herein by reference in its entirety. This application also claims priority to U.S. patent application Ser. No. 13/143,975, now granted as U.S. Pat. No. 8,592,634 (US national phase application of PCT/US2010/021949, filed on Jan. 25, 2010 and entitled "PROCESS FOR PRODUCING PHENOL"), which, in turn, claims priority to U.S. Provisional Patent Application Ser. No. 61/155,746, filed on Feb. 26, 2009 and entitled "PROCESS FOR PRODUCING PHENOL," the contents of both of which are incorporated herein by reference in their entirety.

CROSS REFERENCE TO RELATED APPLICATIONS

This application is related to U.S. Provisional Application Ser. Nos. 61/382,776; 61/382,749; and PCT Application Nos. PCT/US2011/047829; and PCT/US2011/047834.

FIELD

The present invention relates to processes for producing phenol.

BACKGROUND

Phenol is most commonly produced by the Hock process. The Hock process involves alkylation of benzene with propylene to produce cumene, oxidation of the cumene to the corresponding hydroperoxide, and cleavage of the hydroperoxide to produce equimolar amounts of phenol and acetone.

The various steps involved in the production of phenol and acetone from cumene can produce various contaminants that are difficult to separate from the desired phenol and acetone. These contaminants, if left in the phenol product, may cause difficulties in downstream processing, or render the phenol unusable for such downstream processing, for example in the subsequent production of bis-phenols and polycarbonates. Therefore, techniques have been proposed to remove those contaminants involving certain treatments. For example, U.S. Pat. No. 5,064,507 discloses obtaining high purity phenol from cleavage of cumene hydroperoxide through one or more amine treatment steps. The phenol mixture includes at least 0.5 wt % to no greater than 10 wt % of alpha-methylstyrene, and further includes acetol, 2-phenyl-propionaldehyde (2PPA), methyl-benzofuran (MBF), mesityl oxide (MO) and carbonyl impurities. In addition, U.S. Pat. No. 3,322,651 discloses a method of producing phenol made by decomposition of cumene hydroperoxide. The phenol is purified by contacting the carbonyl compounds with a nitrogen compound.

Cyclohexanone is typically produced by the oxidation of cyclohexane, or the hydrogenation of phenol. These methods can also generate various contaminants that are difficult to separate from the desired product, and that can render the cyclohexanone product substandard or unusable to downstream processes, for example in the manufacture of caprolactam or adipic acid, or further using those derivatives in the production of one or another type of nylon. Thus, certain treatment means have been described to remove those contaminants from cyclohexanone. For example, U.S. Pat. No. 7,199,271 discloses a method for reducing the concentration of cyclohexenone in a cyclohexanone-containing organic mixture. The method includes contacting an organic mixture comprising cyclohexenone with an effective amount of at least one of sulfurous acid, a salt of sulfurous acid, an alkali hydroxide, or a mixture of two or more of these compounds.

The production of phenol from cyclohexylbenzene is an emerging technology, interesting in that it co-produces cyclohexanone rather than acetone. Cyclohexylbenzene can be produced, for example, by direct alkylation of benzene with cyclohexene, or as disclosed in U.S. Pat. No. 6,037,513, by contacting benzene with hydrogen in the presence of a catalyst. The cyclohexylbenzene can then be oxidized to the corresponding hydroperoxide and the peroxide cleaved to phenol and cyclohexanone using an acidic cleavage catalyst.

The production of phenol and cyclohexanone from cyclohexylbenzene also produces various contaminants that are difficult to separate from the desired products. However, the nature of those contaminants and the separations involved are significantly different than those involved in either the conventional Hock process for phenol and acetone, or the conventional production of cyclohexanone from cyclohexane or phenol. For example, hydroalkylation of benzene produces significant amounts of, inter alia, cyclohexane and lesser amounts of methylcyclopentane, cyclohexene, phenylcyclohexene, and phenylcyclohexyldiene. Similarly, the oxidation of cyclohexylbenzene typically produces peroxide species alien to the Hock process, such as the desired cyclohexyl-1-phenyl-1-hydroperoxide (CHBHP), and undesired byproduct hydroperoxides such as cyclohexyl-1-phenyl-2-hydroperoxide, cyclohexyl-1-phenyl-3-hydroperoxide and cyclohexyl-1-phenyl-4-hydroperoxide. Finally, the cleavage of these various hydroperoxides produces, as both the product of the undesired hydroperoxides and the undesired byproducts of the desired CHBHP, a wide variety of contaminant species are not produced by the chemistry and technology of either the Hock process, or the cyclohexane oxidation or phenol hydrogenation processes.

Methods are needed to manage the contaminants generated when manufacturing phenol and cyclohexanone from cyclohexylbenzene, and enable the manufacture of high quality phenol or cyclohexanone products.

SUMMARY

In various embodiments, the invention relates to a process for producing phenol, the process comprising: (a) oxidizing at least a portion of a feed comprising cyclohexylbenzene to produce an oxidation composition comprising cyclohexyl-1-phenyl-1-hydroperoxide; (b) cleaving at least a portion of the oxidation composition to produce a cleavage reaction mixture comprising phenol, cyclohexanone and at least one contaminant; and (c) contacting at least a portion of the cleavage reaction mixture with a basic material to convert at least a portion of the contaminant to a converted contaminant, thereby producing a modified reaction mixture.

DETAILED DESCRIPTION

Figure 1:
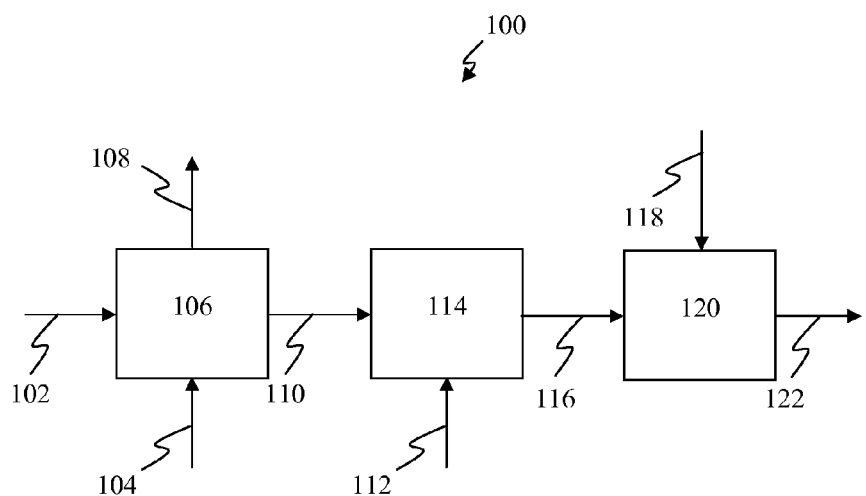
FIG. 1 is a flow diagram of a process for producing phenol that includes conversion of one or more contaminants.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention can be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

The present invention is directed to a process for producing phenol and cyclohexanone from cyclohexylbenzene and, more particularly, to an integrated process for producing phenol and cyclohexanone from benzene via cyclohexylbenzene as an intermediate. In the process the cyclohexylbenzene is initially oxidized to produce an oxidation reaction product comprising cyclohexyl-1-phenyl-1-hydroperoxide and at least a portion of the oxidation reaction product is cleaved to produce a cleavage reaction product comprising phenol, cyclohexanone, and one or more contaminants. Often some or all of the contaminants in the cleavage reaction product are difficult to separate from the phenol and/or cyclohexanone by simple methods, such as distillation. Thus, in the present process, at least a portion of the cleavage reaction product is contacted with a basic material under conditions to convert at least one of the contaminants to a converted contaminant, which is more readily separable from the phenol and/or cyclohexanone.

Production of the Cyclohexylbenzene

In the integrated process for producing phenol and cyclohexanone from benzene, the benzene is initially converted to cyclohexybenzene by any conventional technique, including alkylation of benzene with cyclohexene in the presence of an acid catalyst, such as zeolite beta or an MCM-22 family molecular sieve, or by oxidative coupling of benzene to make biphenyl followed by hydrogenation of the biphenyl. However, in practice, the cyclohexylbenzene is generally produced by contacting the benzene with hydrogen under hydroalkylation conditions in the presence of a hydroalkylation catalyst whereby the benzene undergoes the following reaction (1) to produce cyclohexylbenzene (CHB):

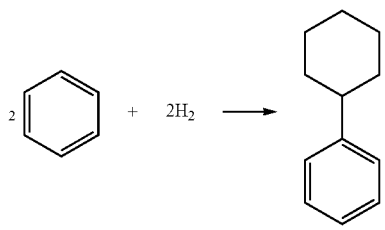

(1)

For an example of hydroalkylation of benzene in the presence of hydrogen for the production of cyclohexylbenzene, see U.S. Pat. Nos. 6,730,625 and 7,579,511 which are incorporated by reference. Also, see International Applications WO2009131769 or WO2009128984 directed to catalytic hydroalkylation of benzene in the presence of hydrogen for the production of cyclohexylbenzene.

Any commercially available benzene feed can be used in the hydroalkylation reaction, but preferably the benzene has a purity level of at least 99 wt %. Similarly, although the source of hydrogen is not critical, it is generally desirable that the hydrogen is at least 99 wt % pure.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes molecular sieves having the MWW framework topology. (Such crystal structures are discussed in the "Atlas of Zeolite Framework Types", Fifth edition, 2001, the entire content of which is incorporated as reference).

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation reaction is highly selective towards cyclohexylbenzene, the effluent from the hydroalkylation reaction will normally contain some dialkylated products, as well as unreacted benzene and the desired monoalkylated species. The unreacted benzene is normally recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, zeolite USY, and mordenite. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 hr$^{-1}$ on total feed, and a benzene/dicyclohexylbenzene weight ratio about of 1:1 to about 5:1.

After removal of the unreacted benzene and the polyalkylated benzenes and other heavy species, the cyclohexylbenzene is fed to the oxidation reaction. Typically, however, this cyclohexylbenzene feed contains the following contaminants generated as by-products of its synthesis:

between 1 wppm and 1 wt % bicyclohexane, or between 10 wppm and 8000 wppm bicyclohexane;
between 1 wppm and 1 wt % biphenyl, or between 10 wppm and 8000 wppm biphenyl;
between 1 wppm and 2 wt % methylcyclopentylbenzene, or between 10 wppm and 1 w % wppm methylcyclopentylbenzene as any isomer: 1-phenyl-1-methylcyclopentane, 1-phenyl-2-methylcyclopentane, and 1-phenyl-3-methylcyclopentane; and
less than about 1000 wppm, such as less than 100 wppm of phenol, olefins or alkylene benzenes, such as cyclohexenyl benzene.

Oxidation Reaction

As discussed above, the process includes oxidizing at least a portion of a feed comprising cyclohexylbenzene to produce an oxidation composition comprising cyclohexyl-1-phenyl-1-hydroperoxide. As used herein, "oxidizing" means causing an oxidation reaction to occur.

The feed comprising cyclohexylbenzene may be produced by any process known to those in the art, and while desirably pure, may contain a small amount of certain byproduct components that are difficult to remove from cyclohexylbenzene, discussed later. The hydroalkylation process may generate byproduct dicyclohexylbenzene, and thus be accompanied by and integrated with the transalkylation of byproduct dicyclohexylbenzene with benzene to produce additional cyclohexylbenzene, and may further include various separations to recover and recycle unreacted benzene, and remove heavy alkylates and other unselective byproducts. Another known method to manufacture a feed comprising cyclohexylbenzene involves the catalytic alkylation of benzene with cyclohexene.

Further, in an embodiment, a portion of the feed comprising cyclohexylbenzene may be a recycle stream comprising cyclohexylbenzene produced by the processing of the treated cleavage reaction mixture, discussed later. In this manner, all or a fraction of cyclohexylbenzene that was unreacted in the oxidation reaction may be recovered and reused to generate additional phenol.

Regardless of the source or sources, in various embodiments, a feed comprising cyclohexylbenzene contains at least about 10 wt %, or at least about 25 wt %, or at least about 50 wt %, or at least about 65 wt %, or at least about 75 wt %, or at least about 95 wt %, or at least about 99 wt % cyclohexylbenzene. In various embodiments, it may contain another component. For example, the feed comprising cyclohexylbenzene may contain at least 1 wppm and no greater than 1 wt % bicyclohexane, or at least 10 wppm and no greater than 8000 wppm bicyclohexane. It may contain at least 1 wppm and no greater than 1 wt % biphenyl, or at least 10 wppm and no greater than 8000 wppm biphenyl. It may contain at least 1 wppm and no greater than 2 wt % methylcyclopentylbenzene, or at least 10 wppm and no greater than 1 w % wppm methylcyclopentylbenzene as any isomer: 1-phenyl-1-methylcyclopentane, 1-phenyl-2-methylcyclopentane, and 1-phenyl-3-methylcyclopentane. There may be other components present, though desirably of low concentration, say, no greater than 1000 wppm, or no greater than 100 wppm of phenol, olefins or alkylene benzenes such as cyclohexenyl benzene, individually or in any combination. For example, in various embodiments, all or a portion of the feed may be subjected to a hydrogenation reaction to hydrogenate at least a portion of one or more of the phenol, olefins and/or alkylene benzenes. The feed comprising cyclohexylbenzene to which oxygen is introduced to cause an oxidation reaction may contain cyclohexylbenzene and any other one component, or any combination of the other components just noted in the proportions for each or in combination just noted.

In various exemplary embodiments, oxidation may be accomplished by contacting oxygen, e.g., (an oxygen-containing gas, such as air and various derivatives of air), with a feed comprising cyclohexylbenzene. For example, one may use air that has been compressed and filtered to removed particulates, air that has been compressed and cooled to condense and remove water, or air that has been enriched in oxygen above the natural approximately 21 mol % in air through membrane enrichment of air, cryogenic separation of air or other means within the ken of the skilled artisan.

The oxidation may be conducted in the absence or presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 wt % to 5 wt %, of the cyclohexylbenzene.

In various embodiments, the oxidation reaction occurs under oxidation conditions. Suitable oxidation conditions include a temperature between about 70° C. and about 200° C., such as about 90° C. to about 130° C., and a pressure of about 50 to 10,000 kPa. A basic buffering agent may be added to react with acidic by-products that may form during the oxidation. In addition, an aqueous phase may be introduced. The reaction can take place in a batch or continuous flow fashion.

Typically, the product of the oxidation of a feed comprising cyclohexylbenzene, i.e., the oxidation composition, contains at least 5 wt %, such as at least 10 wt %, for example at least 15 wt %, or at least 20 wt % cyclohexyl-1-phenyl-1-hydroperoxide based upon the total weight of the oxidation composition. In other manifestations, the oxidation composition contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation composition. The oxidation composition may further comprise imide catalyst and unreacted cyclohexylbenzene. The invention may include cyclohexylbenzene in the oxidation composition in an amount of at least 50 wt %, or at least 60 wt %, or at least 65 wt %, or at least 70 wt %, or at least 80 wt %, or at least 90 wt %, based upon total weight of the oxidation composition.

In addition, the oxidation composition may contain one or more hydroperoxides other than cyclohexyl-1-phenyl-1-hydroperoxide generated as a byproduct of the oxidation reaction of cyclohexylbenzene, or as the oxidation product of some oxidizable component other than cyclohexylbenzene that may have been contained in the cyclohexylbenzene undergoing oxidation. Such oxidizable contaminants include methylcyclopentylbenzenes of various isomers, and bicyclohexane. Other exemplary hydroperoxide contaminants present in the oxidation composition include at least, based on the total weight of the oxidation composition, 0.1 wt % to no greater than 10 wt %, or at least 0.5 wt % to no greater than 5.0 wt %, or at least 1 wt % and no greater than 4 wt % of any one or any combination of: cyclohexyl-1-phenyl-2-hydroperoxide, cyclohexyl-1-phenyl-3-hydroperoxide, cyclohexyl-1-phenyl-4-hydroperoxide; cyclopentyl-1-methyl-2-phenyl-2-hydroperoxide, cyclopentyl-1-methyl-3-phenyl-3-hydroperoxide, cyclopentyl-1-methyl-1-phenyl-2-hydroperoxide, cyclopentyl-1-methyl-1-phenyl-3-hydroperoxide; and cyclohexyl-1-phenyl-1,2-dihydroperoxide, cyclohexyl-1-phenyl-1,3-dihydroperoxide, cyclohexyl-1-phenyl-1,4-dihydroperoxide; cyclopentyl-1-methyl-2-phenyl-1,2-dihydroperoxide, cyclopentyl-1-methyl-2-phenyl-2,3-dihydroperoxide, cyclopentyl-1-methyl-2-phenyl-2,4-dihydroperoxide, and cyclopentyl-1-methyl-2-phenyl-2,5-dihydroperoxide.

The reactor used for the oxidation of cyclohexylbenzene, i.e., the oxidation reactor, may be any type of reactor that allows for introduction of oxygen to cyclohexylbenzene, and may further efficaceously provide contacting of oxygen and cyclohexylbenzene to effect the oxidation reaction. For example, the oxidation reactor may comprise a simple, largely open vessel container with a distributor inlet for the oxygen-containing stream in line. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner well known to those skilled in the art.

At least a portion of the oxidation composition may be subjected to a cleavage reaction, which may include all or some fraction of the oxidation composition as directly produced without undergoing any separation (e.g., some fraction resulting from diverting some amount of the oxidation composition as directly produced to another disposition, such as temporary storage). Thus, the at least a portion of the oxidation composition may have the same composition as the oxidation composition. Further, all or some of the oxidation composition as directly produced may undergo one or more separations, and an appropriate product of that separation (or separations), now modified in composition relative the oxidation composition as directly produced, may provide the at least a portion of the oxidation composition subjected to the cleavage reaction.

For example, all or a fraction of the oxidation composition as directly produced may be subjected to high vacuum distillation, to generate a product enriched in unreacted cyclohexylbenzene relative to the oxidation composition, and the at least a portion of the oxidation composition as a residue concentrated in the desired cyclohexyl-1-phenyl-1-hydroperoxide that may be subjected to a cleavage reaction. Cyclohexylbenzene is essentially a diluent in the cleavage reaction and the neutralization reaction, and further is not a good solvent for most acid catalysts, particularly sulfuric acid. However, distinctive from the Hock process described earlier, it is convenient in the present invention that the at least a portion of the oxidation composition that will undergo the cleavage reaction be of the same composition of cyclohexylbenzene as the oxidation composition directly produced. That is to say, it is convenient that the at least a portion of the oxidation composition undergo no concentration of the hydroperoxide(s) before the acid catalyst is introduced to it, because the starting alkylbenzene cyclohexylbenzene has a significantly higher normal boiling point than the starting alkylbenzene cumene that is found in the Hock process. While within the scope of the present invention, any practical separation attempted to concentrate the cyclohexyl-1-phenyl-1-hydroperoxide or other hydroperoxides from cyclohexylbenzene prior to effecting the cleavage reaction likely requires inconvenient very low vacuum pressure distillation equipment, and even then likely requires very high temperatures that could cause dangerous, uncontrolled thermal decomposition of the hydroperoxides.

Additionally or alternatively, all or a fraction of the oxidation composition, or all or a fraction of the vacuum distillation residue may be cooled to cause crystallization of the unreacted imide oxidation catalyst, which can then be separated either by filtration or by scraping from a heat exchanger surface used to effect the crystallization, and provide an at least a portion of the oxidation composition reduced or free from imide oxidation catalyst that may be subjected to a cleavage reaction.

As another example, all or a fraction of the oxidation composition as produced may be subjected to water washing and then passage through an adsorbent, such as a 3A molecular sieve, to separate water and other adsorbable compounds, and provide an at least a portion of the oxidation composition with reduced water or imide content that may be subjected to a cleavage reaction. Similarly, all or a fraction of the oxidation composition may undergo a chemically or physically based adsorption, such as passage over a bed of sodium carbonate to remove the imide oxidation catalyst (e.g., NHPI) or other adsorbable components, and provide an at least a portion of the oxidation composition reduced in oxidation catalyst or other adsorbable component content that may be subjected to a cleavage reaction. Another possible separation involves contacting all or a fraction of the oxidation composition as produced with a liquid containing a base, such as an aqueous solution of an alkali metal carbonate or hydrogen carbonate, to form an aqueous phase comprising a salt of the imide oxidation catalyst, and an organic phase reduced in imide oxidation catalyst provided as an at least a portion of the oxidation composition that may be subjected to a cleavage reaction. An example of separation by basic material treatment is disclosed in International Application No. WO 2009/025939.

Cleavage Reaction

As discussed above, the process includes cleaving at least a portion of the oxidation composition in the presence of an acid catalyst to produce a cleavage reaction mixture comprising the acid catalyst, phenol and cyclohexanone. As used herein, "cleaving" means causing a cleavage reaction to occur. In the cleavage reaction, at least a portion of the desired cyclohexyl-1-phenyl-1-hydroperoxide will decompose in high selectivity to cyclohexanone and phenol, and further, any other hydroperoxides present will decompose to various products, discussed below.

In various embodiments, the acid catalyst is at least partially soluble in the cleavage reaction mixture, stable at a temperature of at least 185° C. and has a lower volatility (higher normal boiling point) than cyclohexylbenzene. In various embodiments, the acid catalyst is also at least partially soluble in the treated cleavage reaction mixture.

Acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide and sulfur trioxide. Sulfuric acid is a preferred acid catalyst.

In various embodiments, the cleavage reaction mixture contains at least 50 weight-parts-per-million (wppm) and no greater than 3000 wppm of the acid catalyst, or at least 150 wppm to and no greater than 2000 wppm of the acid catalyst, or at least 300 wppm and no greater than 1500 wppm of the acid catalyst, based upon total weight of the cleavage reaction mixture.

In various embodiments of the present invention, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

As a result of potentially high amounts of cyclohexylbenzene in the cleavage reaction mixture, considerably higher than cumene in the Hock process material undergoing a cleavage reaction, it may be convenient in the present invention to use more acid catalyst to effect the cleavage reaction than typically believed optimal in the Hock process, to at least partially overcome the insolubility of the acid in the cleavage reaction mixture. However, lower amounts of acid catalyst may be applied in the present invention, with appropriate additional cleavage reactor volume and residence time of the cleavage reaction mixture in the cleavage reactor to obtain high hydroperoxide conversion.

In various embodiments, the cleavage reaction occurs under cleavage conditions. Suitable cleavage conditions include a temperature of at least 20° C. and no greater than 200° C., or at least 40° C. and no greater than 120° C., and a pressure of at least 1 and no greater than 370 psig (at least 7 and no greater than 2,550 kPa, gauge), or at least 14.5 and no greater than 145 psig (at least 100 and no greater than 1,000 kPa, gauge) such that the cleavage reaction mixture is completely or predominantly in the liquid phase during the cleavage reaction.

Conversion of any hydroperoxide, such as cyclohexyl-1-phenyl-1-hydroperoxide, and conveniently all cyclohexyl-1-phenyl-1-hydroperoxide and other hydroperoxides, is generally very high in the cleavage reaction, e.g., at least 90.0 wt %, or at least 95.0 wt %, or at least 98.0 wt %, or at least 99.0 wt %, or at least 99.5 wt %, or at least 99.9 wt %, or even 100 wt %, the percentage conversion based on the weight of a given specie of hydroperoxide, or of all cyclohexyl-1-phenyl-1-hydroperoxide and other hydroperoxides present in the at least a portion of the oxidation composition undergoing the cleavage reaction. This is desirable because any hydroperoxide, even the cyclohexyl-1-phenyl-1-hydroperoxide, becomes a contaminant in the cleavage reaction mixture and treated cleavage reaction mixture, discussed below. Hydroperoxides cause undesired chemistry when decomposed under uncontrolled conditions outside the cleavage reaction, for if thermally decomposed under the conditions in a distillation column.

The major products of the cleavage reaction of cyclohexyl-1-phenyl-1-hydroperoxide are phenol and cyclohexanone, each of which generally comprise about 40 to about 60 wt %, or about 45 to about 55 wt % of the cleavage reaction mixture, such wt % based on the weight of the cleavage reaction mixture exclusive of unreacted cyclohexylbenzene and acid catalyst.

The cleavage reaction mixture may comprise no greater than 30 wt %, or no greater than 25 wt %, or no greater than about 15 wt % of phenol, or it may comprise at least 1 wt %, or at least 3 wt %, or at least 5 wt %, or at least 10 wt % phenol, based on total weight of the cleavage reaction mixture. Further, the cleavage reaction mixture may comprise no greater than 30 wt %, or no greater than 25 wt %, or no greater than about 15 wt % of cyclohexanone, or it may comprise at least 1 wt %, or at least 3 wt %, or at least 5 wt %, or at least 10 wt % cyclohexanone, based on total weight of the cleavage reaction mixture.

The cleavage reaction mixture may further comprise at least 0.1 and no greater than 10 wt %, or at least 0.5 and no greater than 7 wt %, or at least 1 and no greater than 5 wt %, or at least 1.5 and no greater than 3 wt % of any one or combination of contaminant byproducts based on the total weight of the cleavage reaction mixture.

As used herein, a "contaminant" or a "contaminant byproduct" may include any unwanted hydrocarbon or oxygenated hydrocarbon component in the cleavage reaction mixture or the neutralized cleavage mixture, or any portion of either; that is anything other than phenol, cyclohexanone and cyclohexybenzene. They are unwanted because their presence indicates a decreased yield of desired product phenol and cyclohexanone from cyclohexylbenzene, or they cause difficulties in the separation and purification of phenol, cyclohexanone or unconverted cyclohexylbenzene, or some combination thereof. A contaminant in the cleavage reaction mixture or the neutralized cleavage mixture or any portion thereof may have been produced in any element of the present invention, or may have been contained in the feed comprising cyclohexylbenzene undergoing oxidation. For example, a contaminant may be present in the cleavage reaction mixture as a result of one or more of: (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation composition from (ii).

Examples of contaminants in the cleavage reaction mixture, and possible amounts thereof, include (weight-parts-per-million (wppm) and wt % are based upon total weight of the cleavage reaction mixture):

water, e.g., at least 100 wppm and no greater than 3.0 wt %;

twelve carbon, two ringed hydrocarbons other than cyclohexylbenzene, such as bicyclohexane, cyclohexenylcyclohexane, and cyclohexadienylcyclohexane, cyclohexenylbenzene, cyclohexadienylbenzene and biphenyl, e.g., at least 10 wppm and no greater than 3.0 wt %, each or in total;

saturated and unsaturated ketones, such as pentanones, methylcyclopentanones, hexanones, 1-phenylhexan-1-one and 1-cyclohexylhexan-1-one, phenylcyclohexanones and phenylmethylcyclopentanones, e.g., at least 10 wppm and no greater than 4.0 wt %, each or in total;

cyclohexyldione(s), e.g., at least 10 wppm and no greater than 1.0 wt % in total;

less than 12 carbon, unsaturated hydrocarbons, cyclic and acyclic, or combinations thereof, such as cyclohexene, e.g., at least 10 wppm and no greater than 1.0 wt %, each or in total;

cyclohexanol, e.g., at least 10 wppm and no greater than 1.0 wt %;

cyclohexenone(s), e.g., 2-cyclohexenone or 3-cyclohexenone, e.g., at least 10 wppm and no greater than 2.0 wt %, each or in total;

hydroxycyclohexanone(s), e.g., at least 10 wppm and no greater than 2.0 wt % in total;

carboxylic acids, such as benzoic acid, e.g., at least 10 wppm and no greater than 1.0 wt %, each or in total;

phenyl cyclohexanol(s), e.g., 1-phenylcyclohexan-1-ol, 2-phenylcyclohexan-1-ol, 3-phenylcyclohexan-1-ol and 4-phenylcyclohexan-1-ol, e.g., at least about 10 wppm and no greater than 5.0 wt %, each or in total;

cyclohexyl cyclohexanol(s), such as 1-cyclohexylcyclohexan-1-ol, 2-cyclohexylcyclohexan-1-ol, 3-cyclohexylcyclohexan-1-ol, and 4-cyclohexylcyclohexan-1-ol, e.g., at least 10 wppm and no greater than 1.0 wt %, each or in total;

unsaturated alkyl oxygenated cyclohexanes, such as cyclohexenyl cyclohexanols and cyclohexenyl cyclohexanones, and methylcyclopentenyl cyclohexanols and methylcyclopentenyl cyclohexanones, e.g., at least 10 wppm and no greater than 1.0 wt %, each or in total;

aldehydes, especially, pentanals, hexanals, cyclohexyl or methylcyclopentyl alkyl aldehydes, such 5-cyclohexyl hexanal, and 6-hydroxy-5-cyclohexyl hexanal, e.g., at least 10 wppm and no greater than 1.0 wt %, each or in total;

1-phenyl-6-hydroxyhexan-1-one (also called 6-hydroxyhexanophenone), e.g., at least 10 wppm and no greater than 4.0 wt %;

1-cyclohexyl-6-hydroxyhexan-1-one, e.g., at least 10 wppm and no greater than 1.0 wt %;

benzoic esters, e.g., at least 10 wppm and no greater than 1.0 wt %, each or in total; and a hydroperoxide (e.g., an unreacted hydroperoxide). Non-limiting examples include: the desired cyclohexyl-1-phenyl-1-hydroperoxide, and the other hydroperoxides such as cyclohexyl-1-phenyl-2-hydroperoxide, cyclohexyl-1-phenyl-3-hydroperoxide, cyclohexyl-1-phenyl-4-hydroperoxide; cyclopentyl-1-methyl-2-phenyl-2-hydroperoxide, cyclopentyl-1-methyl-3-phenyl-3-hydroperoxide, cyclopentyl-1-methyl-1-phenyl-2-hydroperoxide, cyclopentyl-1-methyl-1-phenyl-3-hydroperoxide; cyclohexyl-1-phenyl-1,2-dihydroperoxide, cyclohexyl-1-phenyl-1,3-dihydroperoxide, cyclohexyl-1-phenyl-1,4-dihydroperoxide; cyclopentyl-1-methyl-2-phenyl-1,2-dihydroperoxide, cyclopentyl-1-methyl-2-phenyl-2,3-dihydroperoxide, cyclopentyl-1-methyl-2-phenyl-2,4-dihydroperoxide, cyclopentyl-1-methyl-2-phenyl-2,5-dihydroperoxide; e.g., at least 1 wppm and no greater than 1.0 wt %, each or in total.

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

At least a portion of the cleavage reaction mixture may be subjected to a neutralization reaction, which may include all or some fraction of the cleavage reaction mixture as directly produced without undergoing any separation (e.g., some fraction resulting from diverting some amount of the cleavage reaction mixture as directly produced to another disposition, such as temporary storage). Thus, the at least a portion of the cleavage reaction mixture may have the same composition as the cleavage reaction mixture. Further, all or some of the cleavage reaction mixture as directly produced may undergo one or more separations, and an appropriate product of that separation (or separations), now modified in composition relative the cleavage reaction mixture as directly produced, may provide the at least a portion of the cleavage reaction mixture subjected to the neutralization reaction.

Contaminant Treatment

As discussed above, the cleavage reaction mixture may comprise one or more contaminants. In various embodiments disclosed herein, the processes disclosed herein further comprise contacting at least a portion of a contaminant with a basic material to convert at least a portion of the contaminant to a converted contaminant, thereby producing a modified reaction mixture.

Suitable basic materials include alkali and alkali earth metal hydroxides and oxides, such as sodium hydroxide, potassium hydroxide, magnesium hydroxide, calcium hydroxide, calcium oxide and barium hydroxide. Sodium and potassium carbonates may also be used, optionally at elevated temperatures.

In various embodiments, the basic material comprises one or more of: a caustic exchange resin (e.g., sulfonic ion-exchange resin); an alkali metal acetate, an alkali earth metal acetate, an alkali metal carbonate, an alkali earth metal carbonate, an alkali metal bicarbonate, an alkali earth metal bicarbonate, ammonia or ammonium hydroxide; a basic clay such as limestone, dolomite, magnesite, sepiolite and olivine; an activated carbon and/or impregnated activated carbon; an anionic exchange resin, such as a weakly basic ion exchange resin having a styrene-divinyl benzene polymer backbone and an amine functional structure selected from $-N(CH_3)_2$, $-NRH$ or $-NR_2$, where R is a hydrogen or an alkyl group containing 1 to 20 carbon atoms; an amine polysiloxane functionalized with ethylenediamine; an organic basic material grafted on microporous or mesoporous metal oxides; other organo-inorganic solids, such as zeolites exchanged with a metal selected from the group of lithium, sodium potassium, rubidium, cesium, calcium, barium, strontium and radium; an oxide of Group III of the Periodic Table of Elements treated with a metal selected from lithium, potassium, sodium, rubidium and cesium; a supported or solid alkali, alkaline-earth metal or organometallic; a magnesium silicate generally derived from the interaction of a magnesium salt and soluble silicate; a salt with basic hydrolysis such as sodium acetate, sodium bicarbonate, sodium phenate and sodium carbonate; and amine(s), such as a primary, secondary, or tertiary aliphatic amines or aromatic amines, e.g., anilines, n-butyl amine, heterocyclic amines, such as pyridines, piperidines, piperazines, tri-ethyl amine, aliphatic or aromatic diamines and alkanolamines. In particular, amines in the form of their salts with weak organic acids may be used. Conveniently, the basic material is a diamine, such as 2-methylpentamethyenediamine or hexamethylenediamine, which are commercially available from Invista S.àr.l. Corporation under the trade designations DYTEK™ A and DYTEK™ HMD.

The basic material may also be a solid. Suitable solid basic materials include: basic metal oxide families; alkali on metal oxides; alkaline-earth on metal oxides; alkali and alkaline-earth zeolites; transition metals, rare earth and higher valency oxides; hydrotalcites, calcined hydrotalcites and spinels, specifically hydrotalcites treated with an alkali metal selected from lithium, potassium, sodium, rubidium, cesium, and combinations thereof; perovskites; and beta-aluminas.

In one embodiment, the basic material is one or more of the hindered amines described in U.S. Pat. No. 6,201,157. It will be understood that the basic material may be added in the anhydrous state or may be an aqueous solution of any of the foregoing basic materials, particularly the metal hydroxides and salts with basic hydrolysis.

Conveniently, the basic material has a relatively low volatility, with a normal boiling point above phenol and/or cyclohexylbenzene, such that it will tend to distill in the bottoms product in subsequent fractionation operations that may be conducted.

The contaminant treatment can be conducted directly on the cleavage reaction mixture, or after one or more separations of the cleavage reaction mixture. For example, the cleavage reaction mixture may be separated (e.g., by distillation) into phenol-rich and cyclohexanone-rich fractions before or after the contaminants are subjected to contaminant treatment.

Suitable contaminant treatment conditions vary with the basic material employed. Treatment conditions include a temperature of at least about 30° C., or at least about 35° C., or at least about 40° C., or at least about 50° C., or at least about 60° C., or at least about 70° C., or at least about 80° C., or at least about 90° C., or at least about 100° C. In various embodiments, the temperature is less than about 250° C., or less than about 225° C., or less than about 190° C., or less than about 180° C., or less than about 170° C., or less than about 160° C., or less than about 150° C., or less than about 140° C. The temperature may be any range of the aforementioned temperatures.

The pressure may be about 0.75 to about 500 psig (5 kPa to 3450 kPa), or about 10 to 200 psig (70 to 1380 kPa) such that the cleavage reaction mixture is completely or predominantly in the liquid phase during the treatment.

In various embodiments, the pressure may be about 10 to 200 psig (170 to 1380 kPa) and the temperature may be about 60° C. to about 160° C., such that most of the cleavage reaction mixture is in the liquid phase.

In embodiments in which the basic material is a solid microporous material (e.g., zeolites, aluminas, etc.), the pressure may be about 10 to 200 psig (70 to 1380 kPa) and the temperature may be about 100° C. to about 250° C., such that most of the cleavage reaction mixture is in the liquid phase.

In various embodiments in which the basic material is an anion exchange resin (e.g., a quaternary ammonium, such as those commercially available under the trade name Amberlyst™ from Rohm & Haas Company), or an amine polysiloxane functionalized with ethylenediamine, the pressure may be about 10 to 200 psig (70 to 1380 kPa) and the temperature may be about 30° C. to about 100° C., such that most of the cleavage reaction mixture is in the liquid phase.

In various embodiments in which the basic material is an amine, the pressure may be about 1 to 200 psig (5 to about 1380 kPa) and the temperature may be about 30° C. to about 250° C., such that most of the cleavage reaction mixture is in the liquid phase.

In one embodiment, the basic material is a primary amine, which may be particularly useful to remove contaminants containing a ketone group, which will react to form an imine.

It will be understood that the contaminants in all or a portion of the cleavage reaction mixture may be contacted with a basic material as disclosed herein. For example, contaminants in a distilled fraction of the entire cleavage reaction mixture containing an enriched or depleted concentration of phenol and/or cyclohexanone relative to the cleavage reaction mixture may be contacted with a basic material as described herein. When a stream is described as being "rich in" or "enriched" in a specified species, it is meant that the wt % of the specified species in that stream is enriched relative to the feed stream prior to separation. When a stream is described as being "depleted" in a specified species, it is meant that the wt % of the specified species in that stream is reduced relative to the feed stream prior to separation.

Additionally or alternatively, a filtered fraction of the entire cleavage reaction mixture with reduced amounts of filterable components may be contacted with a basic material as described herein.

Additionally or alternatively, a fraction of the cleavage reaction mixture has undergone an absorbtion operation, such as a water wash, such that absorbable components are reduced in concentration prior to contact with a basic material.

Additionally or alternatively, a fraction of the cleavage reaction mixture has undergone an absorption operation, such as passing over a molecular sieve to remove water (e.g., a 3A molecular sieve) with one or more adsorpable components are reduced in concentration prior to contact with a basic material.

The contaminant reactor may be any vessel that allows contacting of the contaminant with a basic material for a suitable residence time. For example, a contaminant reactor may be an open or substantially open vessel reactor or pipe.

In various embodiments, a process for making phenol and cyclohexanone comprises: (i) cleaving a stream comprising cyclohexyl-1-phenyl-1-hydroperoxide in the presence of an acidic cleavage catalyst to produce a cleavage reaction mixture comprising phenol, cyclohexanone, acidic cleavage catalyst, and one or more contaminants; (ii) reacting at least a portion of the acidic cleavage catalyst with a first basic material to form a neutralized stream; (iii) separating the neutralized stream into one or more streams rich in cyclohexanone, phenol and/or cyclohexylbenzene, relative to the neutralized stream; and (iv) contacting one or more of the cyclohexanone-rich portion, the phenol-rich portion, and the cyclohexylbenzene-rich portion with a second basic material to remove one or more contaminants. The first and second basic materials may be the same or different.

In various embodiments, the cleavage reaction mixture is separated into: (1) an overhead product that comprises greater than about 98 wt %, or greater than about 99 wt %, of cyclohexanone, based upon total weight of the overhead product and (2) a bottoms product comprising phenol and cyclohexanone in azeotropic proportion. The impurities contained in the overhead product may include methylcyclopentanone. As used herein, "azeotropic proportion" means about 65-75 wt % phenol and about 23-35 wt % cyclohexanone, or about 72 wt % phenol and about 28 wt % cyclohexanone, based upon total weight of the stream. In various embodiments, a portion or the entire cleavage reaction mixture may be combined with another stream from the overall phenol production process. For example, the cleavage reaction mixture may be combined with a stream containing cyclohexanone produced by the hydrogenation of phenol. Additionally or alternatively, the cleavage reaction mixture may be combined with a stream containing phenol that is produced by the dehydrogenation of cyclohexanone. Additionally or alternatively, the cleavage reaction mixture may be combined with one or more additives, such as an antifoam or surfactant agent.

In various embodiments, contaminants in more than one portion of the cleavage reaction mixture may be contacted with a basic material. For example, the cleavage reaction mixture may be separated into one or more streams rich in cyclohexanone, phenol and/or cyclohexylbenzene, relative to the cleavage reaction mixture and each stream may be contacted with a basic material. The basic material may be the same or different for each fraction.

In various embodiments, a given fraction of the cleavage reaction mixture may undergo more than one contacting steps with a basic material. For example, a cyclohexanone-rich fraction derived from distillation of the entire cleavage reaction mixture may first be contacted with a first basic material (e.g., a diamine) and then separately exposed to a second basic material (e.g., an aqueous solution of sodium hydroxide).

Non-limiting examples of contaminant conversion reactions due to contacting with a basic material include:
  aldol condensation, especially of ketones and aldehydes;
  saponification, especially of esters, making the salt and freeing the alcohol;
  neutralization of acids, making the salt and freeing the water, including complexation, for example, of sodium hydroxide and phenol to make water and sodium phenate;
  iminization, especially of amines/diamines and ketones, for example:

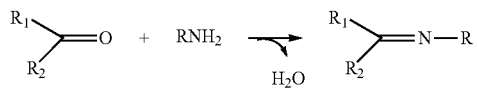

where the contaminant reacts with a phenol molecule;
where the contaminant reacts with a cyclohexanone molecule;
where the contaminant byproduct reacts with another contaminant byproduct of the same or different species; and
any combination of the above.

In various embodiments, the converted contaminants include:
  a property that makes them more separable from phenol and/or cyclohexanone than the starting contaminant. "Separable" can mean distillable, e.g., the converted contaminant does not form an azeotrope with phenol and/or cyclohexanone, whereas the starting contaminant byproduct does; or filterable, or absorbable (e.g., in water or the aqueous basic material), or adsorbable;
  a molecular weight higher than the starting contaminant;
  a molecular weight lower than the starting contaminant;
  a volatility lower than the starting contaminant, and conveniently considerably lower than cyclohexanone and/or phenol;
  a volatility higher than the starting contaminant, conveniently considerably higher than cyclohexanone and/or phenol;
  aldol condensation products, generally aldehydes and ketones;
  water, generally from neutralization of acids;
  alcohols, from saponification of esters;
  acid salts, from a neutralization or saponification reaction; and
  imines, generally of amines/diamines and ketones.

In various embodiments, at least about 20.0%, or at least about 50.0%, or at least about 80.0%, or at least about 90.0%, or at least about 99.9%, or essentially all of any one contaminant is converted to a converted contaminant, based on weight %.

In various embodiments, at least about 20.0%, or at least about 50.0%, or at least about 80.0 5, or at least about 90.0%, or at least about 99.9% of any olefin contaminants, including furans and alcohols, are converted to a converted contaminant, based on weight %.

In various embodiments, at least about 20.0%, or at least about 50.0%, or at least about 80.0%, or at least about 90.0%, or at least about 99.9%, or essentially all of all of the contaminants present in the stream are converted to a converted contaminant, based on weight %.

Processing of Treated Cleavage Reaction Mixture

In various embodiments, after one or more contaminants in the cleavage reaction mixture is contacted with a basic material, the stream may be separated into one or more streams rich in phenol, cyclohexanone and/or cyclohexylbenzene, relative to the feed stream. These streams may be substantially or completely free of contaminants.

In various exemplary embodiments, the process further comprises separating the contaminant-treated stream into a first stream that is enriched in cyclohexanone or phenol or both and a second stream that is enriched in converted contaminant relative to the contaminant-treated stream.

Heat Treatment

In various embodiments, some or all of the contaminants (e.g., in the cleavage reaction mixture or some portion of the cleavage reaction mixture) are subjected to heat treatment conditions upstream or downstream of the contaminant treatment.

For example, the temperature of all or a portion of the cleavage reaction mixture may be raised to at least about 100° C., or about 150° C. to about 185° C., or at least about 200° C. to produce a heat-treated cleavage reaction mixture. In various embodiments, the temperature may be less than about 250° C., or less than about 225° C. The temperature may be any range of the aforementioned temperatures. In various embodiments, the heat treatment conditions include a residence time may be at least 1 min., 2 min., 3 min., 5 min., 10 min., or 15 min. The residence time may be less than about 120 min., 60 min., or 30 min. The residence time may be any logical range of the aforementioned times.

In one embodiment, during heat treatment at least about 1 wt %, or 10.0 wt %, or 20.0 wt %, or 50.0 wt %, or 80.0 wt %, or 90.0 wt %, or 99.0 wt %, or 99.9 wt %, or all of any one contaminant (e.g., hydroxycyclohexanone, or other oxyketones such as hexanophenone, 6-hydroxyhexanophenone, 6-hydroperoxyhexanophenone, benzoic acid, pentanal, pentanone, 2-hydroxycyclohexanone, phenylcyclohexanone, or unreacted peroxides) is converted to a converted contaminant.

In various embodiments, no greater than about 80.0 wt %, or 50.0 wt %, or 30.0 wt %, or 20.0 wt %, or 10.0 wt % of contaminant hydroxycyclohexanone or other oxyketones such as 6-hydroxyhexanophenone, or both are converted to a converted contaminant including a furan with both an olefin and oxygen moiety, such as 1,2,4a,9b-tetrahydrodibenzo[b,d]furan that may result from the dehydration, alkylation and cyclization reaction of phenol and hydroxycyclohexanone.

In various embodiments, the heat-treated stream may be separated into one or more streams rich in one or more of cyclohexanone, phenol and/or cyclohexylbenzene, relative to the heat-treated stream. These fractions may comprise little or no converted contaminants.

The heat treatment may be conducted in a simple vessel or pipe, which may be open or have means for mixing, such as baffles or a static mixer for turbulent flow. Further, the heat treatment may take place in a fractionation column, wherein fractionation operating conditions are selected such that the components distilled are exposed to the temperatures and residence times noted at any point or points in the column. The heat treated components may be withdrawn from any point in the fractionation column, as an overhead, bottoms or side composition product. Generally, the heat treatment converts at least some of the contaminants or converted contaminants to other compounds more readily removed from the phenol and/or cyclohexanone.

After contaminant treatment and/or heat treatment, the converted contaminants will generally have a property that makes them more separable from phenol or cyclohexanone, or both, than the starting contaminant. Separable can be distillable, e.g., the converted contaminant does not form an azeotrope with phenol or cyclohexanone whereas the starting contaminant does, and/or filterable, and/or absorbable. As a result, following contaminant and/or heat treatment, the stream can be subjected to one or more separations ultimately resulting in streams that predominantly comprise cyclohexanone, phenol and converted contaminant.

Neutralization Reaction

In various embodiments, the processes disclosed herein may include neutralizing at least a portion of the cleavage reaction mixture with a basic material to form a treated cleavage reaction mixture. As used herein, "neutralizing" means causing a neutralization reaction to occur. The neutralizing step may occur upstream, downstream or simultaneously with one or more contaminant treatment and/or heat treatment steps.

The conditions at which the neutralization reaction is effected, or neutralization conditions, vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Other suitable neutralization conditions include a temperature of no greater than 200° C., or no greater than 190° C., or no greater than 180° C., or no greater than 170° C., or no greater than 160° C., or no greater than 150° C., or no greater than 140° C., or no greater than 130° C., or no greater than 120° C., or no greater than 110° C., or no greater than 100° C. Further, the neutralization condition temperature may be in any range of the aforementioned temperatures. In various embodiments, the neutralization conditions include a temperature that is reduced from cleavage reaction conditions, for example, the temperature may be 1° C., or 5° C., or 10° C., or 15° C., or 20° C., or 30° C., or 40° C. lower than the temperature of the cleavage reaction.

Suitable neutralization conditions may include about 1 psig to about 500 psig (5 kPa to 3450 kPa, gauge), or about 10 psig to 200 psig (70 kPa to 1380 kPa, gauge) such that the treated cleavage reaction mixture is completely or predominantly in the liquid phase during the neutralization reaction.

The treated cleavage reaction mixture may include cyclohexylbenzene in an amount of at least 50 wt %, or at least 60 wt %, or at least 65 wt %, or at least 70 wt %, or at least 80 wt %, or at least 90 wt %, based upon total weight of the treated cleavage reaction mixture.

The treated cleavage reaction mixture may further comprise at least 0.1 and no greater than 10 wt %, or at least 0.5 and no greater than 7 wt %, or at least 1 and no greater than 5 wt %, or at least 1.5 and no greater than 3 wt % of any one or combination of contaminant byproducts based on the total weight of the cleavage reaction mixture. Example contaminant byproducts and their possible amounts in the treated cleavage reaction mixture are the same as discussed in detail above for the cleavage reaction mixture. In general, a contaminant byproduct in the cleavage reaction mixture will not undergo significant conversion in the neutralization reaction.

In various exemplary embodiments, the neutralization reaction results in the formation of a complexation product, such as an acid-basic material salt. For example, when sulfuric acid is the acid catalyst:

using sodium hydroxide as the basic material, water, and a salt of sodium sulfate, $Na_2SO_4$, is formed that is not soluble in the treated cleavage reaction mixture;

using methylamine as the basic material, a complex of $(CH_3NH_2)_2 \cdot H_2SO_4$ is formed, among other possible complexes, that may be soluble in the treated cleavage reaction mixture; and using hexamethylenediamine as the basic material, complexes of $(H_2N(CH_2)_6NH_2)_2 \cdot H_2SO_4$, among other possible complexes, are formed that are soluble in the treated cleavage reaction mixture.

Conveniently, the complexation product is soluble in the treated cleavage reaction mixture and will stay in the bottoms products of subsequent distillations of at least a portion of the treated cleavage reaction mixture, thus eliminating the need for additional separations to remove the complexation product from the at least a portion of the treated cleavage reaction mixture.

Conveniently, the complexation product has a low volatility, with a normal boiling point above phenol or cyclohexylbenzene, such that it will tend to distill in the bottoms product of subsequent fractionation operations that may be conducted on the at least a portion of the treated cleavage reaction mixture containing the complexation product.

Conveniently, the complexation product has a high thermal stability and does not dissociate or otherwise decompose at high temperatures associated with subsequent processing of the neutralized cleavage product, particularly distillation, such as at least about 300° C., or at least about 275° C., or at least about 250° C., or at least about 225° C., or at least about 200° C.

The complexation product may be substantially inert to the other components in the treated cleavage reaction mixture or other streams derived therefrom, such as cyclohexanone, phenol, cyclohexylbenzene, contaminants and/or mixtures thereof.

When basic material is introduced to the at least a portion of the cleavage reaction mixture and the neutralization reaction occurs, some or all of acid catalyst and basic material are transformed to complexation product. Introducing basic material at a point prior to perfect stoichiometric complexation or reaction (i.e., acid catalyst is still the excess reactant), the treated cleavage reaction mixture will have a reduced content of acid catalyst relative to the at least a portion of the cleavage reaction mixture undergoing the neutralization reaction, and is depleted of basic material, potentially none. Introducing basic material at just the point of perfect stoichiometric complexation or reaction, the treated cleavage reaction mixture will be depleted of acid catalyst relative to the at least a portion of the cleavage reaction product, potentially none, and also is depleted of basic material relative to the at least a portion of the cleavage reaction product, potentially none. Introducing basic material past the point of perfect stoichiometric complexation or reaction (i.e., basic material is now the excess reactant), the treated cleavage reaction mixture will have a reduced content of acid catalyst relative to the at least a portion of the cleavage reaction product, potentially none, but will have a content of basic material increasing in proportion to the amount of basic material introduced. As noted earlier, a complexation product, though potentially comprising each acid catalyst and basic material specie, is neutralized and generally inert. An uncomplexed specie, or unreacted specie in the case of a more definitive reaction such as sodium hydroxide with sulfuric acid, is capable of undergoing or catalyzing various types of chemistry, desired and undesired. Further, it is possible that both the acid catalyst and the basic material are present in the treated cleavage reaction mixture, even with one or the other in excess of stoichiometry, due to imperfect mixing in or insufficient residence time of the cleavage reaction.

In various embodiments, basic material is introduced to the at least a portion of the cleavage reaction mixture to form a treated cleavage reaction mixture that contains no greater than 150 wppm of the acid catalyst, or no greater than 100 wppm, or no greater than 50 wppm, or no greater than 25 wppm, or no greater than 10 wppm, or no greater than 2 wppm of the acid catalyst, based upon total weight of the treated cleavage reaction mixture. Additionally or alternatively, basic material is introduced to the at least a portion of the cleavage reaction mixture to form a treated cleavage reaction mixture that contains no greater than 150 wppm of the basic medium, or no greater than 100 wppm, or no greater than 50 wppm, or no greater than 25 wppm, or no greater than 10 wppm, or no greater than 2 wppm of the basic medium, based upon total weight of the treated mixture. Lower contents of both acid catalyst and basic material in the treated cleavage reaction mixture are desirable, as either constituent will cause adverse reactions of the desired cyclohexanone and phenol products in subsequent separation and purification operations using at least a portion of the treated cleavage reaction mixture, particularly in distillation columns.

The amount of basic material introduced to the at least a portion of the cleavage reaction mixture to obtain a given level of acid catalyst or basic material in the neutralized cleavage reaction product is highly dependent on and varies widely with both the acid catalyst and the basic material selected, and, of course, the amount of acid catalyst in the at least a portion of the cleavage reaction mixture.

Further, the techniques for measurement of the amount of basic material or acid catalyst in a largely or exclusively organic matrix such as a treated cleavage reaction mixture are also quite specific to both the acid catalyst and the basic material selected, and the nature of the organic matrix. The typical method for such measurement in aqueous systems is the determination of a pH value using various methods, as the classical definition of pH is related to hydrogen ion activity in a highly aqueous matrix. Conventional methods of and instruments used in the determination of pH are based on a highly aqueous matrix, and the pH value they provide on hydrogen ion activity is directly related and converted to acid or base concentration in the aqueous matrix. However, while such conventional pH methods and instruments may provide pH readings for an organic matrix, such readings cannot be readily related or converted to acid or base concentration as they are in an aqueous matrix.

To overcome this problem of the measurement of the amount of basic material or acid catalyst in a largely or exclusively organic matrix such as a treated cleavage reaction mixture, one may employ what is herein termed a "calibrated method." A calibrated method is a conventional pH method further developed to correlate the reading that conventional pH method or instrument may provide to a given amount of acid catalyst or basic material content in an organic matrix based on the specific acid catalyst, basic material and organic matrix of interest.

Two fundamental approaches are available to develop calibrated methods for organic matrices based on conventional pH methods and instruments, and thus determine the acid catalyst and basic material concentration in an organic matrix such as a treated cleavage reaction mixture. The first involves dilution of an aliquot of the organic matrix in a large quantity of a highly hydrogen bonded composition, generally including water or an alcohol, or both. For example, in the pH measurement of phenol for use in DNA experiments in the biochemical industry, a reported method includes mixing 2 ml of the organic phase with 5 ml of methanol and 13 ml of water, then measuring the pH of the entire sample. The pH measurement thereby obtained has been correlated to some property of the undiluted phenol matrix, such as the ability of the phenol to have DNA to partition into the organic, phenolic phase. This is assigned in the biochemical industry as being an "acidic" phenol, though acidic in that case does not have the classic meaning as being acidic in a conventional aqueous system.

The second fundamental approach to develop a calibrated method for organic matrices based on conventional pH methods and instruments is a direct measurement of the voltage generated by a standard hydrogen electrode, also known as a "pH probe." A pH probe measures the liquid junction potential between the sample of interest and the electrode's electrolyte laden filling reference solution, and double-junction reference electrodes are also well known in the art. Typical electrolytes employed with the reference solution include potassium chloride and other organic or inorganic salts. In conventional pH methods and instruments, the matrix being measured and the reference solution are aqueous; however, when the matrix being measured is organic, the reference solution is also organic, typically of very similar materials as the organix matrix and comprising an appropriate organic salt, and optionally a minor amount of water. Again, the voltage value that will be provided by such a pH probe in an organic matrix with an organic reference solution cannot be generally and directly translated to hydrogen activity and acid and base concentration as is often the case with an aqueous matrix, but rather has been specifically correlated to some property of the organic matrix of interest, such as the concentration of an acid catalyst or a basic material.

There are permutations and combinations of these fundamental approaches, for example, using a pH probe on a diluted aliquot of organic sample.

In any approach to developing a calibrated method for determining the amount of basic material or acid catalyst in an organic matrix, the reading or measurement value only has meaning when the instrument and method employed has been specifically correlated to the property of interest. For example, with regard to a pH probe, one may consult U.S. Pat. No. 5,066,373, wherein a titration curve for a double-junction reference electrode pH probe is developed based on adding known amounts of acid and base to an organic matrix of phenol, acetone and cumene; the reference solutions comprise a suitable organic matrix of phenol, acetone and cumene, and an electrolyte of a tetralkyl- or a tetraarylammonium salt. The titration curve is developed by recording the voltage generated by the pH probe at various concentrations of acid and base, generally by starting with an organic matrix free of either and assigning the voltage measured as "neutral," that is, comprising no or virtually no unreacted or uncomplexed specie of acid catalyst or basic material. Then acid is added in increments to the neutral organic matrix and the voltage recorded, and such voltages and correlated to discrete, precise concentrations of acid. Such voltages may arbitrarily be assigned a lower pH value, though again, this is not pH in the classic defintion in aqueous systems. Then base is added to the acidic organic matrix (the organic matrix is titrated) in increments and the voltage recorded, and such voltages are correlated to discrete, precise concentrations of acid with respect to the previously obtained voltages until the voltage passes through the neutral point. Base is then added beyond the neutral point and the voltage recorded and such voltages and correlated to discrete, precise concentrations of base. Such voltages may arbitrarily be assigned a higher pH value, though once again, this is not pH in the classic defintion in aqueous systems.

In the instant invention, a calibrated method of determining the amount of acid catalyst or basic material in the treated cleavage reaction mixture may developed. This may involve either fundamental approach to methods and instruments discussed herein, wherein a titration curve is developed to correlate a specific, measured pH value (for example using pH paper on a diluted aliquot of organic sample), or voltage measurement (for example using a pH probe on an undiluted sample of organic matrix), to a specific amount of acid catalyst or basic material in a treated cleavage reaction mixture. Typically the titration curve will be developed with an organic matrix comprising cyclohexylbenzene, phenol and cyclohexanone. In one specific embodiment, the starting organic matrix for developing the titration curve for a calibrated method comprises 80 wt % cyclohexylbenzene, 10 wt % phenol and 10 wt % cyclohexanone. Such a starting organic matrix, if used as a reference solution in a double-junction pH probe, may further comprise a suitable electrolyte, such as 0.02 wt % or 0.03 wt % of a tetraalkyl- or tetrarlyammonium salt, such as tetraphenylammonium chloride or tetramethylammonium bromide, and optionally a minor amount of water, say 1 wt %, these percentages being with respect to the overall mixture (the organic matrix percentage figures should maintain the aforementioned proportions though their absolute value may be reduced somewhat by the salt or the water).

The calibrated method of choice to determine the amount of acid catalyst or basic material in the treated cleavage reaction mixture may be employed in this invention on a continual basis, that is, determined periodically on a regular frequency. Direct (undiluted) measurements using pH probes are convenient for such continual determination, and this may even be employed continuously to provide an analog signal of voltage. However, diluted approaches of various types will also suffice to allow continual determination on a useful frequency. In one embodiment, the continually determined amount of the acid catalyst and basic material in the treated cleavage reaction mixture can continually be compared to a target amount, and a difference between the determined and target amount similarly continually determined. The introduction of basic material to the cleavage reaction mixture can then be adjusted appropriately based on this continually determined difference to reduce the difference and more closely approach the target amount of acid catalyst and basic material. This continual determination and adjustment may be conducted with a suitable automated control system, wherein a computer (i) receives a signal from a calibrated method instrument that it correlates to an amount of acid and base in the treated cleavage reaction mixture, (ii) calculates the difference based on a manually input target amount, and (iii) for example, should the difference value indicates there is more acid than the target amount, increases the introduction of basic material by an amount proportional to the difference via increasing the opening of a control valve in a line that introduces basic material.

In various embodiments, contacting the basic material and the at least a portion of the cleavage reaction mixture is conducted in a reactor, the neutralization reactor. The neutralization reactor may be any vessel that allows contacting of the acid catalyst with a basic material for a suitable residence time. For example, the neutralization reactor may be an open or substantially open vessel reactor or pipe. The neutralization reaction is exothermic, but generally the amount of acid catalyst and basic material reacting is small relative to the overall amount of treated cleavage reaction mixture, and heat management is not a particular concern for the neutralization reactor.

In various embodiments, contacting the basic material and the at least a portion of the cleavage reaction mixture in the neutralization reactor occurs for a suitable residence time to enable stoichiometric or near stoichiometric conversion of the acid catalyst and basic material species, according the prevailing chemical kinetics of the acid catalyst and basic material species at the neutralization conditions employed in the present invention. In various embodiments, the residence time is at least 0.01 and no greater than 30 minutes, or at least 0.05 and no greater than 20 minutes, or at least 1 and no greater than 5 minutes.

At least a portion of the treated cleavage reaction mixture may be subjected to a processing, which may include all or some fraction of the treated cleavage reaction mixture as directly produced without undergoing any separation (e.g., some fraction resulting from diverting some amount of the treated cleavage reaction mixture as directly produced to another disposition, such as temporary storage). Thus, the at least a portion of the treated cleavage reaction mixture may have the same composition as the treated cleavage reaction mixture. Further, all or some of the treated cleavage reaction mixture as directly produced may undergo one or more separations, and an appropriate product of that separation (or separations), now modified in composition relative the treated cleavage reaction mixture as directly produced, may provide the at least a portion of the treated cleavage reaction mixture subjected to the neutralization reaction.

In various embodiments, the invention relates to: (a) oxidizing at least a portion of a feed comprising cyclohexylbenzene to produce an oxidation composition comprising cyclohexyl-1-phenyl-1-hydroperoxide; (b) cleaving at least a portion of the oxidation composition to produce a cleavage reaction mixture comprising phenol, cyclohexanone and at least one contaminant; and (c) contacting at least a portion of the cleavage reaction mixture with a basic material to convert at least a portion of the contaminant to a converted contaminant, thereby producing a modified reaction mixture.

It will be understood by one skilled in the art that the oxidation composition may undergo one or more actions between (a) and (b) that alter the composition. For example, one or more feed streams and/or recycle streams may be added to the oxidation composition. Additionally or alternatively, the composition may be heated, and/or one or more separations and/or purifications may be performed on the oxidation composition. It is intended that such altered compositions be included within the definition of "oxidation composition."

Similarly, the cleavage reaction mixture may undergo one or more actions between (b) and (c) that alter the composition. It is intended that such altered compositions be included within the definition of "cleavage reaction mixture."

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam and nylons, such as nylon 6 and nylon 6,6.

The phenol produced through the processes disclosed herein may be used, for example, to produce phenolic resins, bisphenol A, ∈-caprolactam, adipic acid and/or plasticizers.

Description According to the Figures

FIG. 1 illustrates an exemplary process 100 for producing phenol and cyclohexanone. As shown, line 102 comprising cyclohexylbenzene is provided to oxidation reactor 106. Line 104 comprising oxygen (e.g., air) is also provided to oxidation reactor 106. As the oxidation reaction continues, oxygen is depleted and an oxygen depleted stream is removed from oxidation reactor 106 via line 108. In accordance with various exemplary embodiments, line 102 comprises at least about 10 wt %, or at least about 25 wt %, or at least about 50 wt %, or at least about 75 wt %, or at least about 95 wt %, or at least about 99 wt % of cyclohexylbenzene, based upon total weight of the stream.

Cyclohexylbenzene hydroperoxide (e.g., cyclohexyl-1-phenyl-1-hydroperoxide) is provided via line 110 to cleavage reactor 114. An acid catalyst (e.g., sulfuric acid) is also provided to cleavage reactor 114 via line 112. Conditions in cleavage reactor 114 are such that a cleavage reaction takes place, causing the cyclohexyl-1-phenyl-1-hydroperoxide and any other hydroperoxides and dihydroperoxide present to decompose to phenol, cyclohexanone and contaminants. A cleavage reaction mixture including phenol, cyclohexanone, acidic cleavage catalyst and one or more contaminants, is withdrawn from cleavage reactor 114 in line 116.

The cleavage reaction mixture in line 116 is directed to contaminant reactor 120, which contains a basic material (e.g., amine, or a diamine, such as 2-methylpentamethylenediamine) provided via line 118. Contaminant reactor 120 may be any device suitably correlated to the basic material utilized therein. In the embodiment depicted in FIG. 1, basic material is not provided by a separate line to the contaminant reactor 120. Such an embodiment is representative of, for example, a solid basic material. In this instance, contaminant reactor 120 filled with the solid in a manner conducive to fixing the solid in the vessel and the reactor dimensions and quantity of solid is such that it provides the desired contacting residence time at the given conditions. In various embodiments, the contaminants may be affixed to the solid medium and remain in contaminant reactor 120, and the solid basic material may be used until it loses effectiveness and then replaced.

In another embodiment not shown in FIG. 1, the basic material may be a liquid aqueous basic material, for example, aqueous sodium hydroxide and contaminant reactor 120 may be a countercurrent wash column, or a liquid-liquid extraction column or countercurrent series of liquid-liquid contacting drums. In such an embodiment, lines not shown in FIG. 1 may be present carrying the fresh liquid basic material into, and the used liquid basic material out of, contaminant reactor 120.

Figure 2:
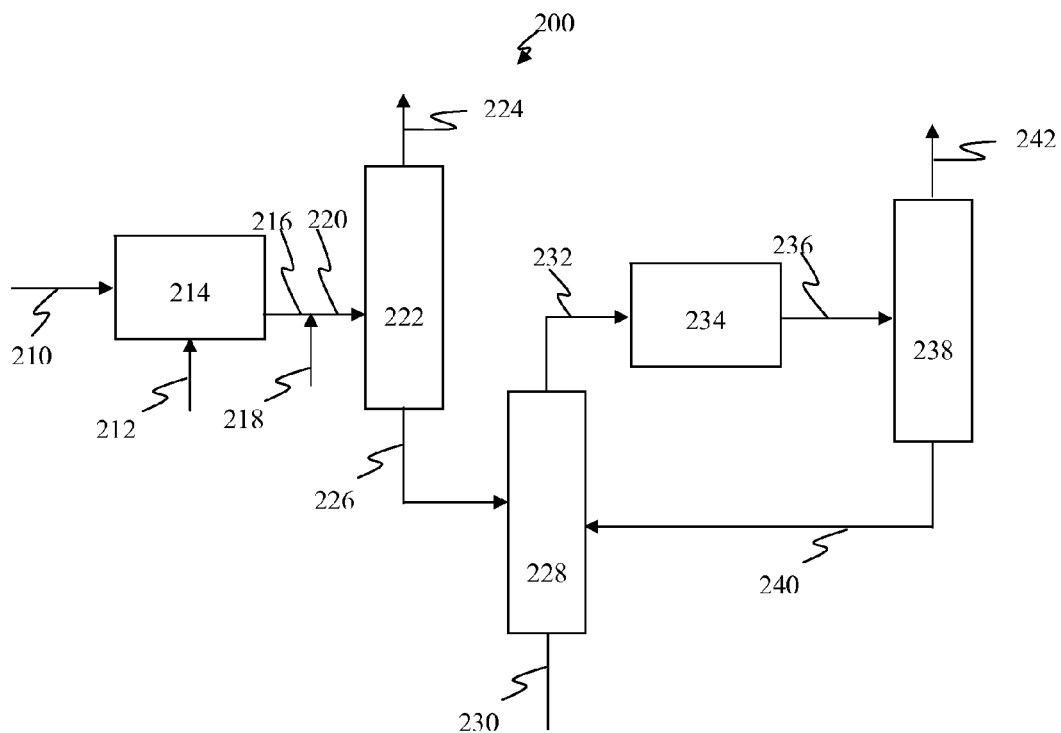
FIG. 2 is a flow diagram of a process for producing phenol that includes conversion of one or more contaminants and separation of the converted contaminant from the desired phenol and cyclohexanone products.

FIG. 2 illustrates an exemplary process 200 for producing phenol and cyclohexanone. Process 200 comprises supplying cyclohexylbenzene hydroperoxide by line 210 to cleavage reactor 214, which also receives an acidic cleavage catalyst via line 212. Conditions in cleavage reactor 214 are such that a cleavage reaction takes place, causing the cyclohexylbenzene hydroperoxide and any other hydroperoxides and dihydroperoxides to decompose to phenol, cyclohexanone and contaminants. A cleavage reaction mixture including phenol, cyclohexanone, acidic cleavage catalyst and contaminants, is withdrawn from cleavage reactor 214 as a cleavage reaction mixture in line 216.

Line 216 is mixed with a basic material (e.g., 2-methylpentane-1,5-diamine), supplied via line 218 to complex with and neutralize the acidic cleavage catalyst, creating a neutralized product stream 220, which also comprises phenol, cyclohexanone, one or more contaminants and complexation products (i.e., formed during neutralization) that are conveniently soluble in the balance of the substantially neutralized stream and further have a relatively low volatility compared to cyclohexylbenzene. In one embodiment, an excess of the basic material is supplied in line 218 beyond the stoichiometric neutralization of the acidic cleavage catalyst in line 216 to give the substantially neutralized product in line 220 a more basic character.

Line 220 is provided to first separator 222 (e.g., fractionation column) which provides a first overhead product in line 224 that is enriched in material having a higher volatility than cyclohexanone (e.g., methylcyclopentanone) relative to at least a portion of the neutralized product stream in line 220, and is depleted in cyclohexanone, phenol, cyclohexylbenzene and other lower volatility components relative to at least a portion of the neutralized product stream in line 220. First separator 222 also provides a first bottoms product in line 226 that is rich in cyclohexanone and lower volatility components relative to the neutralized product stream in line 220, and further includes contaminants that are difficult to fractionate from cyclohexanone and phenol, and depleted of material with a higher volatility than cyclohexanone, relative to the neutralized product stream in line 220. Further, the first bottoms product in line 226 is rich in, and conveniently contains all of, the complexation product introduced into first separator 222 in line 220.

The first bottoms product in line 226 is provided to second separator 228 (e.g., a distillation column), which is operated to provide a second overhead product in line 232 that is rich in cyclohexanone relative to at least a portion of the first bottoms product in line 226 and further includes contaminants, and is depleted of phenol, cyclohexylbenzene, lower volatility components, and converted contaminants, relative to at least a portion of the first bottoms product in line 226. Second separator 228 is operated to also provide a second bottoms product in line 230 that is rich in cyclohexylbenzene and lower volatility components relative to at least a portion of line 226, and conveniently comprises phenol and cyclohexanone in azeotropic proportion. Further, the second bottoms product in line 230 is rich in, conveniently containing all of, the complexation product introduced to second separator 228 in the first bottoms product in line 226.

The second overhead product in line 232 is directed to contaminant reactor 234. Contaminant reactor 234 contains a basic material, and conditions are such that at least a portion of a contaminant is converted to a converted contaminant. Line 236 containing a reduced amount of contaminants relative to that provided with the second overhead product inline 232 is removed from contaminant reactor 234.

Contaminant reactor 234 may be any vessel suitably correlated to the basic material utilized therein. Line 236 containing a reduced amount of the contaminant and enriched in products that are less volatile than cyclohexanone, is directed to third separator 238, which is operated to provide a third overhead product in line 242 that is rich in cyclohexanone, and is depleted of contaminants and converted contaminants relative to the product contained in line 236. Third separator 238 is also provides a third bottoms product in line 240 that is rich in converted contaminants, and is depleted of cyclohexanone relative to the product contained line 236. In one embodiment, the third bottoms product in line 240 contains sufficient cyclohexanone to carry within it some of the contaminants that may not have undergone purification in contaminant reactor 234.

The third bottoms product in line 240 containing converted contaminants and optionally cyclohexanone is also provided to second separator 228. In this manner, any cyclohexanone present in the third bottoms product in line 240 will be recovered in the second overhead product in line 232, and the converted contaminants will be removed in the second bottoms product in line 230. Alternatively, not shown in FIG. 2, the third bottoms product in line 240 containing converted contaminants and possibly cyclohexanone is not provided to second separator 228, but instead directed to alternative processing, used for fuel, or discarded.

With further reference to FIG. 2, the first separator 222, and/or of second separator 228 may be operated to expose contaminants therein to a temperature for a residence time (i.e., heat treatment conditions), to convert at least a portion of the contaminants into a second purification product of lower volatility than cyclohexanone, of phenol, or of both. Optionally, the heat treatment may be enhanced by an additive, such as a substoichiometric addition of an amine with volatility lower than cyclohexylbenzene. The second purification product then exits the separation columns with the first bottoms product in line 226, or the second bottoms product in line 230, or both.

As will be understood by those skilled in the art, the methods of the present invention may utilize numerous equipment and unit operation elements not shown in the Figures or discussed in their description, including but not limited to, heat exchangers through which streams may pass to decrease or increase their temperatures prior to being introduced into another element, as well as pumps and compressors to provide motive force for streams, mixers, instrumentation and control valves.

In addition, although the Figures illustrate continuous processes, batch operations (e.g., with intermittent introduction and removal of streams), or semi-batch operations (e.g., with some streams are intermittently introduced and removed and some streams are continuously removed) are within the scope of the present invention.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

Additionally or alternately, the invention can be described by the following embodiments:

1. A process for producing phenol comprising:
   (a) oxidizing at least a portion of a feed comprising cyclohexylbenzene to produce an oxidation composition comprising cyclohexyl-1-phenyl-1-hydroperoxide;
   (b) cleaving at least a portion of the oxidation composition to produce a cleavage reaction mixture comprising phenol, cyclohexanone and at least one contaminant; and
   (c) contacting at least a portion of the cleavage reaction mixture with a basic material to convert at least a portion of the contaminant to a converted contaminant, thereby producing a modified reaction mixture.
2. The process of 1, wherein the contaminant is one or more of an acyclic aliphatic hexanal, an acyclic aliphatic hexanone, a cyclohexenone, a cyclohexyldione, a hydroxycyclohexanone, benzoic acid, a benzoic ester, a cyclohexenyl cyclohexanone, a methylcyclopentenyl cyclohexanone, 1-phenyl-6-hydroxyhexan-1-one, 1-cyclohexyl-6-hydroxyhexan-1-one, and a bicyclic twelve carbon hydroperoxide.
3. The process of 1, wherein the basic material is one or more of an alkali metal hydroxide, an alkali earth metal hydroxide, alkali metal acetate, an alkali earth metal acetate, an alkali metal carbonate, an alkali earth metal carbonate, an alkali metal bicarbonate, an alkali earth metal bicarbonate, ammonia, a basic clay, an anionic exchange resin, an activated carbon, and an amine
4. The process of 1, wherein the basic material is a primary, secondary or tertiary amine
5. The process of 1, wherein the basic material is a diamine
6. The process of 1, wherein the contacting (c) is conducted at a temperature of about 30° C. to about 250° C. and a pressure of about 5 to about 3450 kPa.
7. The process of 6, wherein the contacting (c) is conducted at a temperature of about 60° C. to about 160° C. and a pressure of about 170 to about 1380 kPa.
8. The process of 1, wherein the contaminant is formed during the oxidizing (a).
9. The process of 1, wherein the contaminant is formed during the cleaving (b).
10. The process of 1, wherein the cyclohexylbenzene is produced by contacting benzene with hydrogen in the presence of a bifunctional catalyst.

11. The process of 10, wherein the bifunctional catalyst is a zeolite of the MCM-22 family containing at least one metal selected from palladium, ruthenium, nickel, zinc, tin and cobalt.

12. The process of 10, wherein the contaminant is formed in the production of the cyclohexylbenzene and is provided with the feed comprising cyclohexylbenzene in (a).

13. The process of 1, further comprising:
heating at least a portion of the at least one contaminant upstream of the contacting (c) to a temperature of at least 100° C. to produce a heat-treated cleavage reaction mixture comprising the at least one contaminant.

14. The process of 1, further comprising:
separating at least a portion of the modified reaction product into a first stream rich in at least one of cyclohexanone and phenol relative to the modified reaction product, and a second stream rich in the converted contaminant relative to the modified reaction product.

15. The process of 1, further comprising:
separating at least a portion of the cleavage reaction mixture upstream of the contacting (c) to provide a cyclohexanone-rich fraction containing at least a portion of the contaminants and providing the contaminants in the cyclohexanone-rich fraction to the contacting step (c).

16. The process of 1, further comprising:
separating at least a portion of the cleavage reaction mixture to provide at least a phenol-rich fraction containing at least a portion of the contaminants, and providing the contaminants in the phenol-rich fraction to the contacting step (c).

17. Phenol produced by the process of embodiment 1.

18. Cyclohexanone produced by the process of embodiment 1.

19. At least one of a phenolic resin, bisphenol A, ε-caprolactam, an adipic acid or a plasticizer produced from the phenol of embodiment 17.

20. At least one of adipic acid, a cyclohexanone resin, a cyclohexanone oxime, caprolactam or nylon produced from the cyclohexanone of embodiment 18.

21. A process for producing phenol comprising:
(a) contacting oxygen and a feed comprising cyclohexylbenzene to cause an oxidation reaction to occur and produce an oxidation composition comprising cyclohexyl-1-phenyl-1-hydroperoxide;
(b) contacting an acid catalyst and at least a portion of the oxidation composition to cause a cleavage reaction to occur, and produce a cleavage reaction mixture comprising phenol, cyclohexanone and at least one contaminant; and
(c) contacting a basic material and at least a portion of the cleavage reaction mixture to convert at least a portion of the contaminant to a converted contaminant, thereby producing a modified reaction mixture.

22. A process for producing phenol comprising:
(a) oxidizing cyclohexylbenzene to produce an oxidation composition comprising cyclohexyl-1-phenyl-1-hydroperoxide;
(b) cleaving at least a portion of the cyclohexyl-1-phenyl-1-hydroperoxide to produce a cleavage reaction mixture comprising phenol, cyclohexanone and at least one contaminant; and
(c) contacting at least a portion of the contaminant with a basic material to convert at least a portion of the contaminant to a converted contaminant, thereby producing a modified reaction mixture.

23. A process for producing phenol comprising:
(a) cleaving a stream comprising cyclohexyl-1-phenyl-1-hydroperoxide in the presence of an acidic cleavage catalyst to produce a cleavage reaction mixture comprising phenol, cyclohexanone, acidic cleavage catalyst and one or more contaminants;
(b) neutralizing at least a portion of the acidic cleavage catalyst with a first basic material to form a second stream;
(c) separating the second stream in a first separator to provide: (i) a first overhead product that is rich in material with a higher volatility than cyclohexanone; and (ii) a first bottoms product that is rich in cyclohexanone;
(d) separating the first bottoms product in a second separator to provide: (i) a second overhead product that is rich in cyclohexanone and the one or more contaminants; and (ii) a second bottoms product that comprises phenol and cyclohexanone;
(e) contacting at least a portion of the one or more contaminants in the second overhead product with a second basic material to convert at least a portion to one or more converted contaminants and thereby produce a modified reaction product;
(f) separating the modified reaction product in a third separator to provide: (i) a third overhead product that is rich in cyclohexanone and is depleted of the one or more contaminants; and (ii) a third bottoms product that is rich in the one or more contaminants and is depleted of cyclohexanone; and
(g) recycling at least a portion of the third bottoms product to the second separator.

24. The process of 23, wherein one or more of the first separator, second separator and third separator are operated at heat treatment conditions.

25. The process of 23, wherein an additive is added to one or more of the first separator, second separator and third separator.

26. The process of 23, wherein the additive is an amine having a lower volatility than cyclohexylbenzene.

27. The process of any one of 23, wherein the first basic material and the second basic material are the same.

28. The process of any one of 23, wherein the first basic material and the second basic material are different, and the second basic material is an aromatic primary amine 29. A process for producing phenol comprising:
(a) hydroalkylating benzene to produce at least some cyclohexylbenzene;
(b) oxidizing at least a portion of the cyclohexylbenzene to produce at least some cyclohexyl-1-phenyl-1-hydroperoxide;
(c) cleaving at least a portion of the cyclohexyl-1-phenyl-1-hydroperoxide to produce a cleavage reaction mixture comprising phenol, cyclohexanone and at least one contaminant; and
(d) contacting at least a portion of the at least one contaminant with a basic material to convert at least a portion to a converted contaminant.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:
1. A process for producing phenol and/or cyclohexanone comprising:
(a) oxidizing at least a portion of a feed comprising cyclohexylbenzene to produce an oxidation composition comprising cyclohexyl-1-phenyl-1-hydroperoxide;

(b) cleaving at least a portion of the oxidation composition to produce a cleavage reaction mixture comprising phenol, cyclohexanone and one or more contaminants; and (c) contacting at least a portion of the cleavage reaction mixture comprising a combined concentration of contaminants of at least 0.1 wt % and no greater than 10 wt %, based on the total weight of the portion of the cleavage reaction mixture, with a basic material to convert at least a portion of the one or more contaminants, thereby producing a modified reaction mixture;

wherein the basic material is one or more of an anionic exchange resin, an activated carbon, and a diamine.

2. The process of claim 1, wherein the contaminant is one or more of an acyclic aliphatic hexanal, an acyclic aliphatic hexanone, a cyclohexenone, a cyclohexyldione, a hydroxycyclohexanone, benzoic acid, a benzoic ester, a cyclohexenyl cyclohexanone, a methylcyclopentenyl cyclohexanone, 1-phenyl-6-hydroxyhexan-1-one, 1-cyclohexyl-6-hydroxyhexan-1-one and a bicyclic twelve carbon hydroperoxide.

3. The process of claim 1, wherein the contacting (c) is conducted at a temperature of about 30° C. to about 250° C. and a pressure of about 5 to about 3450 kPa.

4. The process of claim 1, wherein the contacting (c) is conducted at a temperature of about 60° C. to about 160° C. and a pressure of about 170 to about 1380 kPa.

5. The process of claim 1, wherein the contaminant is formed during the oxidizing (a).

6. The process of claim 1, wherein the contaminant is formed during the cleaving (b).

7. The process of claim 1, wherein the cyclohexylbenzene is produced by contacting benzene with hydrogen in the presence of a bifunctional catalyst.

8. The process of claim 7, wherein the bifunctional catalyst is a zeolite of the MCM-22 family containing at least one metal selected from palladium, ruthenium, nickel, zinc, tin and cobalt.

9. The process of claim 7, wherein the contaminant is formed in the production of the cyclohexylbenzene and is provided with the feed comprising cyclohexylbenzene in (a).

10. The process of claim 1, further comprising:
heating at least a portion of the at least one contaminant upstream of the contacting (c) to a temperature of at least 100° C. to produce a heat-treated cleavage reaction mixture comprising the at least one contaminant.

11. The process of claim 1, further comprising:
separating at least a portion of the modified reaction mixture into a first stream rich in at least one of cyclohexanone and phenol relative to the modified reaction product, and a second stream rich in contaminant relative to the modified reaction product.

12. The process of claim 1, further comprising:
separating at least a portion of the cleavage reaction mixture upstream of the contacting (c) to provide a cyclohexanone-rich fraction containing at least a portion of the contaminants and providing the contaminants in the cyclohexanone-rich fraction to the contacting step (c).

13. The process of claim 1, further comprising:
separating at least a portion of the cleavage reaction mixture to provide at least a phenol-rich fraction containing at least a portion of the contaminants, and providing the contaminants in the phenol-rich fraction to the contacting step (c).

14. A process for producing phenol and/or cyclohexanone comprising:
(a) contacting oxygen and a feed comprising cyclohexylbenzene to cause an oxidation reaction to occur and produce an oxidation composition comprising cyclohexyl-1-phenyl-1-hydroperoxide;

(b) contacting an acid catalyst with at least a portion of the oxidation composition to cause a cleavage reaction to occur, and produce a cleavage reaction mixture comprising phenol, cyclohexanone and at least one contaminant, wherein the combined concentration of contaminants in the cleavage reaction mixture is at least 0.1 wt % and no greater than 10 wt %, based on the total weight of the cleavage reaction mixture; and (c) contacting a basic material with at least a portion of the cleavage reaction mixture to convert at least a portion of the one or more contaminants, thereby producing a modified reaction mixture;

wherein the basic material is one or more of an anionic exchange resin, an activated carbon, and a diamine.

15. A process for producing phenol and/or cyclohexanone comprising:
(a) oxidizing cyclohexylbenzene to produce an oxidation composition comprising cyclohexyl-1-phenyl-1-hydroperoxide;

(b) cleaving at least a portion of the cyclohexyl-1-phenyl-1-hydroperoxide to produce a cleavage reaction mixture comprising phenol, cyclohexanone and one or more contaminants, wherein the combined concentration of contaminants in the cleavage reaction mixture is at least 0.1 wt % and no greater than 10 wt %, based on the total weight of the portion of the cleavage reaction mixture; and (c) contacting at least a portion of the contaminant with a basic material to convert at least a portion of the contaminant, thereby producing a modified reaction mixture;

wherein the basic material is one or more of an anionic exchange resin, an activated carbon, and a diamine.

* * * * *